(12) United States Patent
Courtney et al.

(10) Patent No.: US 9,668,777 B2
(45) Date of Patent: *Jun. 6, 2017

(54) PEDICLE SCREW FIXATION SYSTEM AND METHOD FOR USE OF SAME

(71) Applicant: Eminent Spine LLC, Georgetown, TX (US)

(72) Inventors: Steve Courtney, Plano, TX (US); David Freehill, Temple, TX (US)

(73) Assignee: Eminent Spine LLC, Georgetown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,948

(22) Filed: Dec. 6, 2016

(65) Prior Publication Data

US 2017/0079688 A1 Mar. 23, 2017

Related U.S. Application Data

(63) Continuation of application No. 14/606,657, filed on Jan. 27, 2015, now Pat. No. 9,510,869, which is a continuation of application No. 14/072,600, filed on Nov. 5, 2013, now Pat. No. 8,940,031, which is a continuation of application No. 12/629,585, filed on Dec. 2, 2009, now Pat. No. 8,574,274.

(60) Provisional application No. 61/119,312, filed on Dec. 2, 2008.

(51) Int. Cl.
*A61B 17/70* (2006.01)
*A61B 17/86* (2006.01)

(52) U.S. Cl.
CPC ...... *A61B 17/7034* (2013.01); *A61B 17/7037* (2013.01); *A61B 17/8605* (2013.01); *A61B 17/8685* (2013.01)

(58) Field of Classification Search
CPC ............ A61B 17/7034; A61B 17/7035; A61B 17/7037; A61B 17/7032
See application file for complete search history.

(56) References Cited

U.S. PATENT DOCUMENTS

| 6,010,503 A | 1/2000 | Richelsoph et al. |
| 6,740,086 B2 | 5/2004 | Richelsoph |
| 6,843,791 B2 | 1/2005 | Serhan |

(Continued)

OTHER PUBLICATIONS

ISR PCT/US2009/066426, Jan. 26, 2010.

*Primary Examiner* — Eduardo C. Robert
*Assistant Examiner* — Julianna N Harvey
(74) *Attorney, Agent, or Firm* — Scott T. Griggs; Griggs Bergen LLP

(57) ABSTRACT

A pedicle screw fixation system and method for use of the same are disclosed. In one embodiment, a tulip is provided for holding a head of a pedicle screw substantially along a longitudinal axis. The tulip includes opposing first and second U-shaped receiving slots aligned along a transverse axis. A rod is received by the opposing first and second U-shaped receiving slots. A coupling collar includes a plurality of resilient fingers circumferentially disposed therearound such that a snap fit engagement with the head of the pedicle screw formed. The coupling collar includes a first deformable face operable for contact with the rod. A set screw is for adapted for driving engagement through the tulip along the longitudinal axis such that a second deformable face is positioned for contact with the rod. The first and second deformable faces conform to the shape of the rod in response to forceful engagement therewith.

18 Claims, 5 Drawing Sheets

(56) References Cited

U.S. PATENT DOCUMENTS

| | | |
|---|---|---|
| 7,211,086 B2 | 5/2007 | Biedermann et al. |
| 7,942,907 B2 | 5/2011 | Richelsoph |
| 8,574,274 B2 | 11/2013 | Courtney et al. |
| 8,940,031 B2 | 1/2015 | Courtney et al. |
| 9,510,869 B2 | 12/2016 | Courtney et al. |
| 2002/0143341 A1 | 10/2002 | Biedermann et al. |
| 2004/0225289 A1 | 11/2004 | Biedermann |
| 2007/0055240 A1 | 3/2007 | Matthis et al. |
| 2008/0287998 A1 | 11/2008 | Doubler et al. |
| 2010/0023061 A1 | 1/2010 | Randol et al. |
| 2010/0049255 A1 | 2/2010 | Matthis et al. |
| 2010/0152787 A1 | 6/2010 | Walsh et al. |
| 2010/0198272 A1 | 8/2010 | Keyer et al. |
| 2010/0262196 A1 | 10/2010 | Barrus et al. |
| 2011/0054546 A1 | 3/2011 | Abdelgany |

PEDICLE SCREW FIXATION SYSTEM AND METHOD FOR USE OF SAME

PRIORITY STATEMENT & CROSS-REFERENCE TO RELATED APPLICATIONS

This application is a continuation of U.S. patent application Ser. No. 14/606,657 entitled "Pedicle Screw Fixation System and Method for Use of Same", filed on Jan. 27, 2015 and issued on Dec. 6, 2016 as U.S. Pat. No. 9,510,869, in the names of Steve Courtney and David Freehill; which is a continuation of U.S. patent application Ser. No. 14/072,600 entitled "Pedicle Screw Fixation System and Method for Use of Same", filed on Nov. 5, 2013, and issued on Jan. 27, 2015 as U.S. Pat. No. 8,940,031, in the names of Steve Courtney and David Freehill; which is a continuation of U.S. patent application Ser. No. 12/629,585 entitled "Pedicle Screw Fixation System and Method for Use of Same," filed on Dec. 2, 2009, and issued on Nov. 5, 2013 as U.S. Pat. No. 8,574,274 in the names of Steve Courtney and David Freehill; which claims priority from 61/119,312 entitled "Pedicle Screw Fixation System and Method for Use of Same" and filed on Dec. 2, 2008 in the names of Steve Courtney and David Freehill; all of which are hereby incorporated by reference for all purposes.

TECHNICAL FIELD OF THE INVENTION

This invention relates, in general, to connection of an orthopedic rod to an anchoring element and, in particular, to a pedicle screw fixation system and method for use of the same for surgical use on the spinal column of a patient for stabilization thereof.

BACKGROUND OF THE INVENTION

A large number of pedicle screws for fixation of the spinal column are already known. The disadvantages of these pedicle screws includes the relatively complicated locking mechanisms for securing the orthopedic rod into a receiving member or tulip. In many cases, the head of the pedicle screw can be aligned with the position of the orthopedic rod only to a limited extent, necessitating complicated bending of the longitudinal bar to correct the angle. Alternatively, the tulips are pivotly mounted to the head of the pedicle screw by way of a universal joint providing pivoting linkage therebetween. These pivoting linkages, while permitting the alignment of the orthopedic rod, have proven themselves to lack the rigidity required during surgery to achieve and maintain an accurate placement.

SUMMARY OF THE INVENTION

A pedicle screw fixation system and method for use of the same are disclosed. In one embodiment, a tulip is provided for holding a head of a pedicle screw substantially along a longitudinal axis in a pivoting linkage providing polyaxial placement. The tulip includes opposing first and second U-shaped receiving slots aligned along a transverse axis. A rod is received by the opposing first and second U-shaped receiving slots. A coupling collar includes a plurality of resilient fingers circumferentially disposed therearound such that a snap fit engagement with the head of the pedicle screw formed therebetween. The coupling collar includes a first deformable face operable for contact with the rod. A set screw is adapted for driving engagement through the tulip along the longitudinal axis such that a second deformable face is positioned for contact with the rod. The respective first and second deformable faces conform to the shape of the rod in response to forceful engagement therewith; thereby, increasing the surface area of contact therebetween and locking the tulip in position relative to the pedicle screw.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
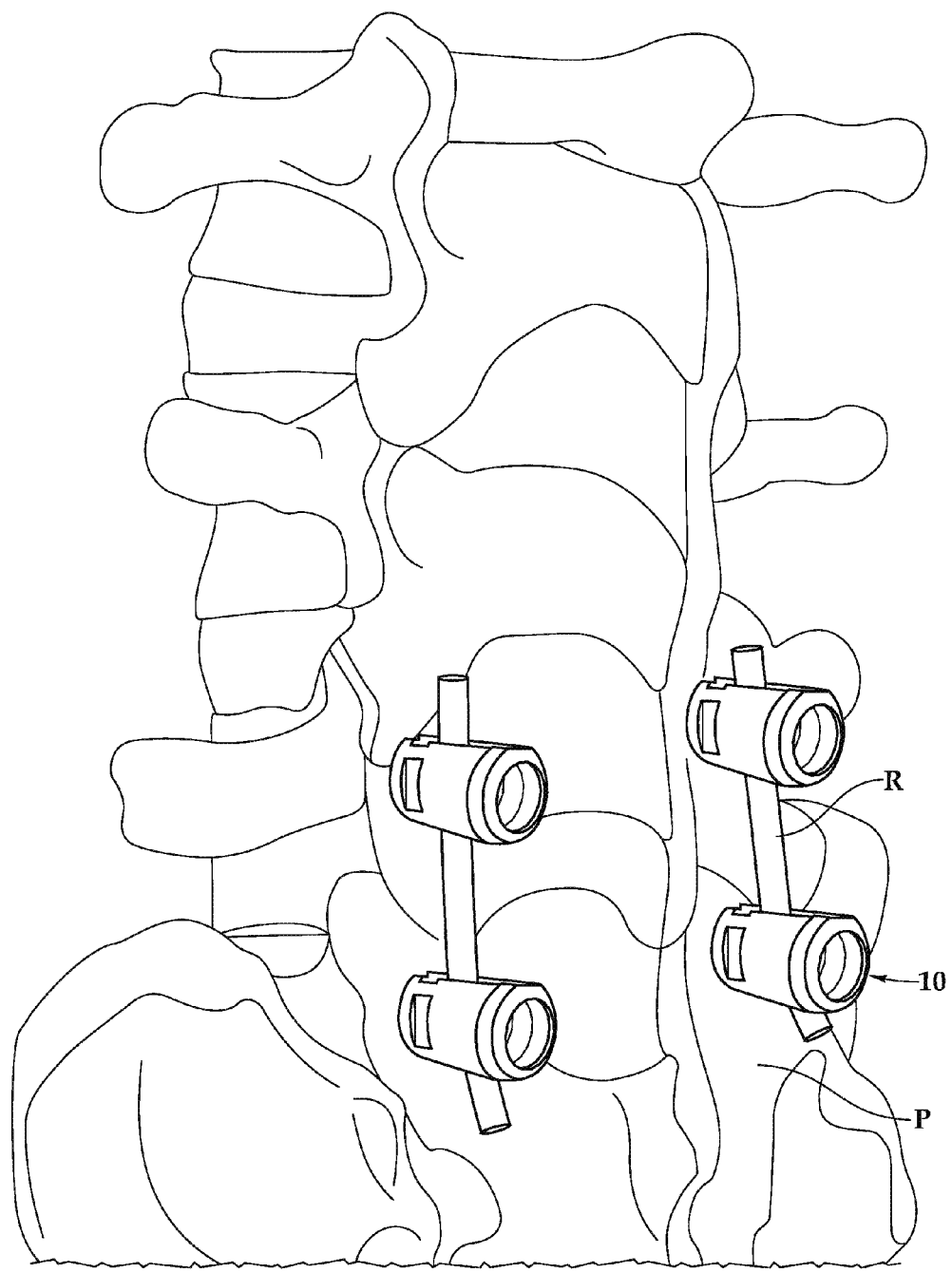
FIG. 1 is an illustrated view of one embodiment of a set of pedicle screw fixations systems implanted into a human vertebral column.
Figure 2:
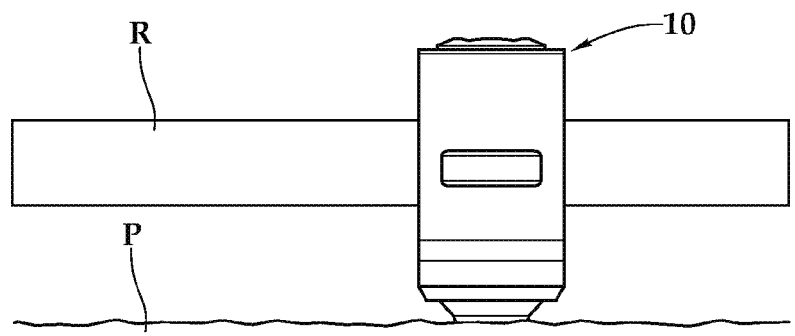
FIG. 2 is a side view of the pedicle screw fixation system of FIG. 1 implanted into the human vertebral column.

Referring initially to FIGS. 1 and 2, therein is depicted one embodiment of a set of pedicle screw fixation systems, individually and collectively numbered 10, implanted into a humane vertebral column. A vertebral pedicle is a dense stem-like structure that projects from the posterior of a vertebra. There are two pedicles per vertebra that connect to other structures such as lamina and vertebral arches. By way of example, the pedicle screw fixation system presented herein may be used to correct deformity, treat trauma, or a combination thereof. Additionally, such pedicle screw fixation systems may be used in instrumentation processes to affix rods and plates to the spine or, alternatively, they may be used to immobilize part of the spine to assist fusion by holding bony structures together.

As shown in FIG. 1 and FIG. 2, the pedicle screw fixation systems 10 are placed down the small bony tube created by the pedicle, which is represented by the letter P, on each side of the vertebra, between the nerve roots. This allows the pedicle screw fixation system 10 to grab into the bone of the vertebral body, furnishing a solid hold in the vertebra. As illustrated, rods, such as orthopedic rod or rod R, connect the pedicle screw fixation systems 10 together at two or more consecutive spine segments, such as lumbar segments 5 and 6.

Figure 3:
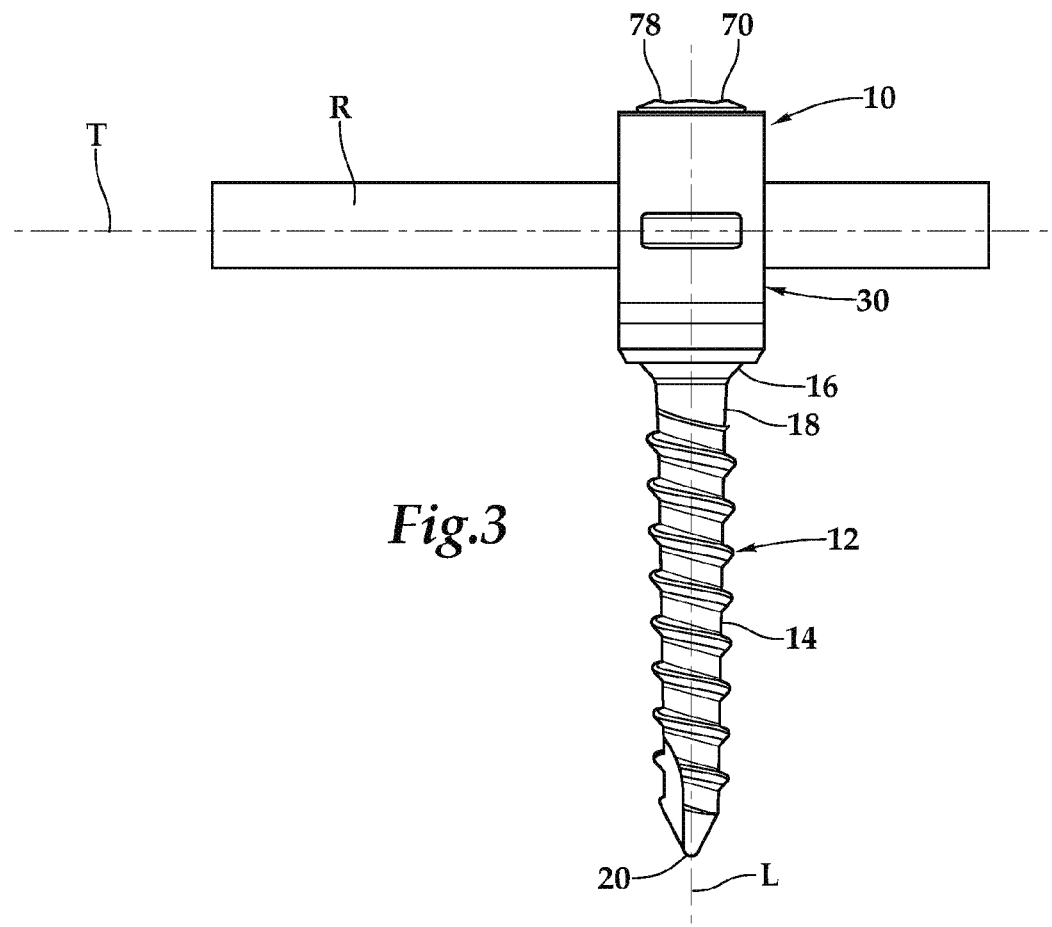
FIG. 3 is a side elevation view of the pedicle screw fixation system depicted in FIG. 2, wherein for purposes of illustration the pedicle screw fixation system is not shown implanted into a human vertebral column.
Figure 4:
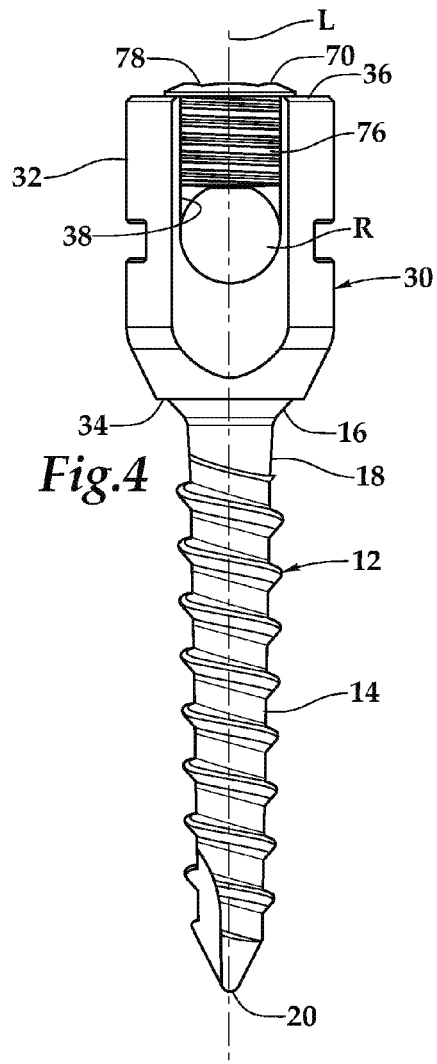
FIG. 4 is a second side elevation view of the pedicle screw fixation system depicted in FIG. 2, the view of FIG. 3 being 90° displaced from the view of FIG. 3.
Figure 5:
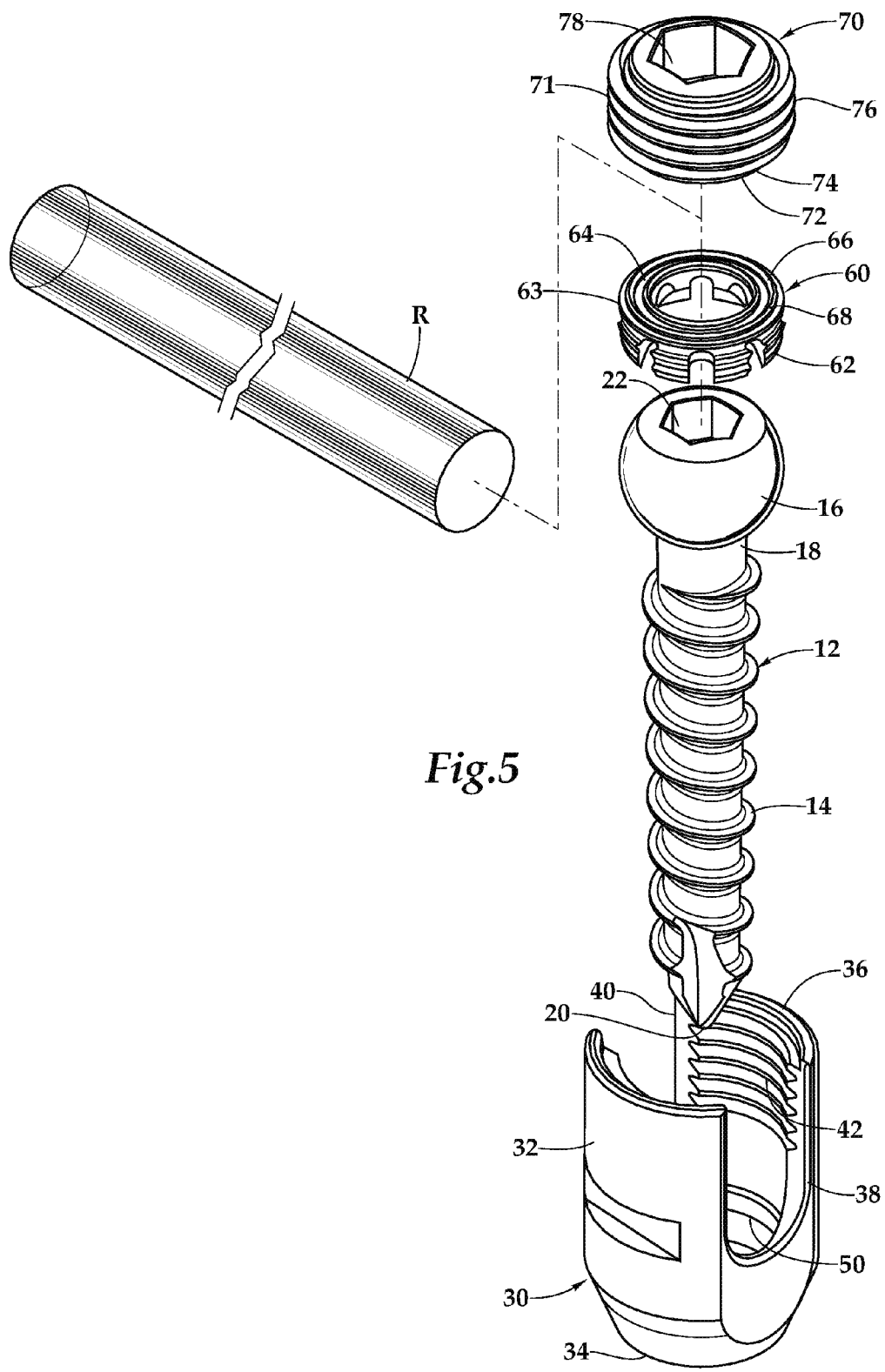
FIG. 5 is a perspective exploded view of the pedicle screw system depicted in FIG. 2.

Referring now to FIG. 3 through FIG. 5, therein is depicted one embodiment of the pedicle screw fixation system 10 and rod R in further detail. A pedicle screw 12 includes a threaded shaft 14 and a spherically-shaped head 16 integrally formed therewith at a shank 18. In one implementation, a contact point 20 at the end of the threaded shaft 14 includes an inclined plane. A socket 22 is located on the head of the pedicle screw.

A tulip 30 in the form of a receiving member includes a housing 32 for receiving the pedicle screw 12 that is defined by a housing bore 34 on one end of a longitudinal axis L and an opening 36 on the other end of the longitudinal axis L. Two opposing U-shaped receiving slots 38, 40 intersect the opening 36 and are aligned along a traverse axis T, which is orthogonal to the longitudinal axis L. Internal threads 42 span the portion of the housing 32 between the receiving slots 38, 40. The pedicle screw 12 is adapted to be inserted through the opening 36 and the housing bore 34 along the longitudinal axis L of the tulip 30. A spherical-shaped seat 50 is formed proximate to the housing bore 34 to accept the head 16 of the pedicle screw 12 and provide a universal point of contact 52 having a receiving space 54 (see FIGS. 10 and 11) thereabout to permit some angular displacement of the tulip 30 about the pedicle screw 12. In one embodiment, the universal point of contact 52 provides a pivoting linkage for polyaxial placement of the pedicle screw 12 relative to the tulip 30.

The head 16 of the pedicle screw 12 is located in contact with the interior of the tulip 30 and, in one embodiment, the shape of the head 16 conforms to the shape of the seat 50. The pivotal linkage formed between the head 16 and the housing 32 of the tulip 30 provides the rigidity required during surgery to achieve and maintain an accurate placement. This universal joint does not reposition with a minimum or accidental amount of force, rather an intentional amount of force is required for positioning and repositioning. It should be appreciated that although the shape of the head 16 and the shape of the seat 50 are illustrated as being complimentary spherical shapes, other shapes, including conical and pyramidal shapes, for example, are within the teachings presented herein.

Figure 6:
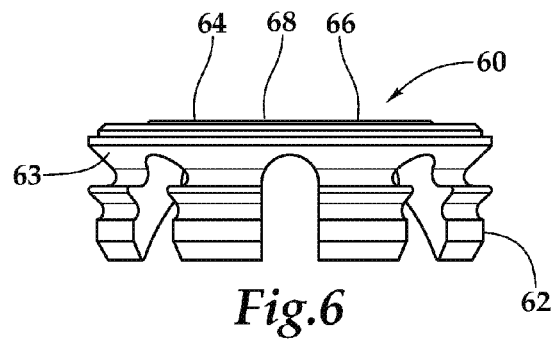
FIG. 6 is a top perspective view of one embodiment of a component, a coupling collar, of the pedicle screw system depicted in FIG. 2.
Figure 7:
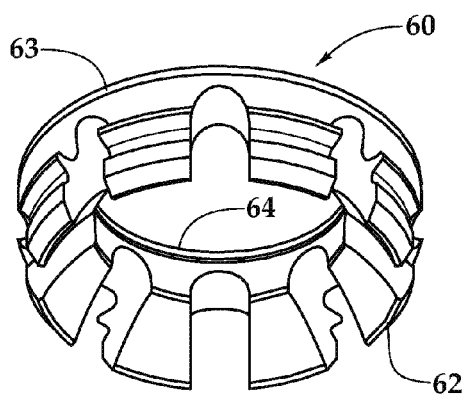
FIG. 7 is a bottom perspective view of the component depicted in FIG. 6.

FIG. 6 and FIG. 7 depict a coupling collar 60 that includes a plurality of resilient fingers 62 circumferentially disposed about a body 63. The resilient fingers 62 provide for a snap fit engagement with the head 16 of the pedicle screw 12. A window 64 in the coupling collar extends therethrough to furnish access to the socket 22. A deformable face 66 is presented by the coupling collar 60 toward the opening 36. In one embodiment, a pair of collapsible rings 68 create the deformable face 66. The coupling collar 60 not only provides a surface of engagement as will be discussed in further detail below, the coupling collar 60 protects the head 16 and socket 22 from damaging torque and force during installation of the pedicle screw fixation system 10.

Figure 8:
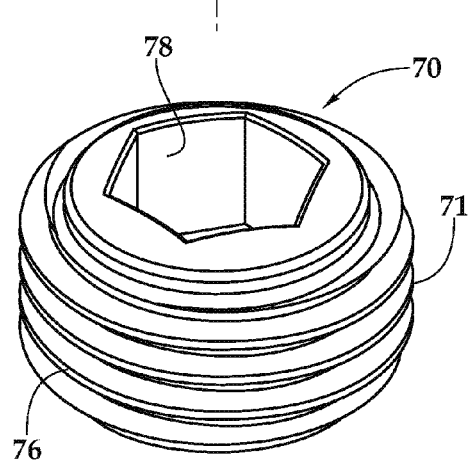
FIG. 8 is a top perspective view of one embodiment of a component, a set screw, of the pedicle screw system depicted in FIG. 2.
Figure 9:
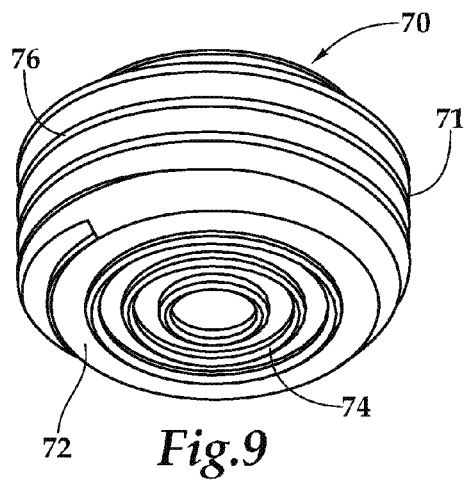
FIG. 9 is a bottom perspective view of the component depicted in FIG. 8.

FIG. 8 and FIG. 9 depict a driving member or in one specific embodiment, the set screw 70 that threadably engages the internal threads 42. A lower end of a body 71 of the set screw 70 presents a deformable face 72 opposite to the deformable face 66 of the coupling collar 60. Three collapsible 74 rings create this second deformable face 72. The upper end of the set screw 70 also includes a socket 78 for accepting the application of torque from a tool, such as an Allen wrench. Additionally, the sides of the set screw include threads 76 that are adapted to mate with the internal threads 42 of the tulip 30.

Although a set screw is depicted, it should be appreciated that the driving member may be any mechanical device that engagingly travels along the longitudinal axis L of the pedicle screw fixation system 10 to apply force or torque to secure or lock the rod. With respect to the coupling collar 60 and the set screw 70, these components are configured to be positioned within the housing 32. Each of the coupling collar 60 and the set screw 70 define respective contact surfaces that are deformable in response to the application of torque and contact between the respective contact surfaces and the rod R. Such application of force increases the surface area of the contact surfaces in contact with the outer surface of the rod R. In one embodiment, as shown, these contact surfaces are smooth. It should be appreciated that these contact surfaces may be roughed, serrated, ribbed, otherwise finished and profiled to improve the engagement between the contact surfaces and the rod R. Similarly, it should be understood that although a smooth rod is depicted, the rod may be correspondingly roughed, serrated, ribbed or otherwise finished and profiled to further improve frictional engagement between the contacts surfaces of the coupling collar 60 and the set screw 70 and the rod 70.

In one embodiment, the coupling collar 60 and the set screw 70 are configured to be positioned within the housing 32 such that the coupling collar 60 is beneath rod receiving space 80 and the set screw is above rod receiving space 80. The rod receiving space 80 also being formed by the housing 32. In this embodiment, the rod receiving space 80 of the housing 32 is interposed between the coupling collar 60 and the set screw 70. In response to the application of force, the coupling collar 60 and the set screw 70, or diving member, undergo a plastic deformation of metal and change form to more complement a contour of the outer surface of the rod R. In this manner, the coupling collar 60 and the set screw 70 expand into the rod receiving space 80 not occupied by the rod R. More particularly, the coupling collar 60 and the set screw 70 may expand into the receiving space 54 and the receiving space 82.

Figure 10:
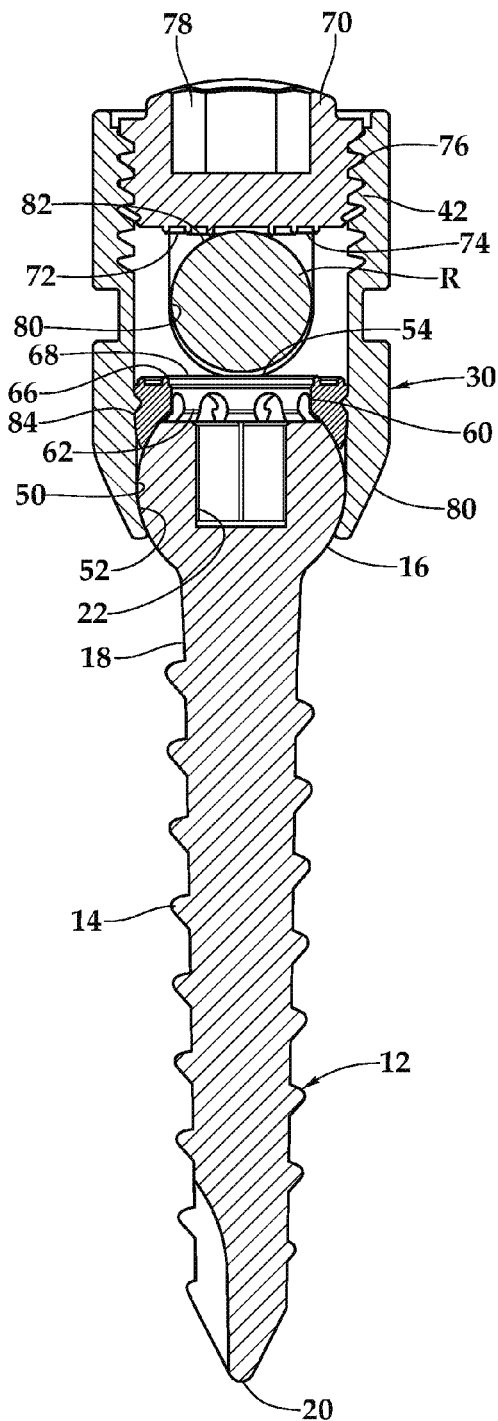
FIG. 10 is a side cross-sectional view of the pedicle screw system depicted in FIG. 2 prior to application of force.

Referring now to FIG. 10, in operation, the threaded portion of the pedicle screw 12 may be secured to a bone by first drilling a pilot hole into the bone and then inserting the tip end or contact point 20 of the threaded portion into the pilot hole. More particularly, the surgeon may use fluoroscopy, conventional x-ray, computer-assisted visualization or another technique to determine the depth and angle for the screw placement. A receiving channel is drilled and the screw is inserted. As mentioned, the head 16 of the pedicle screw 12 is moveable, allowing it to swivel so as to defray vertebral stress.

The pedicle screw 12 provides a firm anchor points that can then be connected to the rod R. A tool or driver, such as an Allen wrench, is then inserted through the window 64 in the coupling collar 60 into the socket 22 formed in the pedicle screw head. After the pedicle screw 12 is torqued and securely anchored into the bone, the tulip 30 is free to pivot and rotate relative to the pedicle screw 12 so that the orthopedic rod R may be positioned through the receiving slots 38, 40 and seated therein in contact with the coupling collar 60. The orthopedic rod R may be tubular without any threads. After the orthopedic rod R is positioned, the set screw 70 is threadably engaged with the internal threads 42 of the tulip 30 and driven toward the orthopedic rod R until the lower end of the set screw 70 engages the orthopedic rod R. As shown, the coupling collar 60 is positioned in a conformed fit 84 with the seat 50 of the tulip 30.

Figure 11:
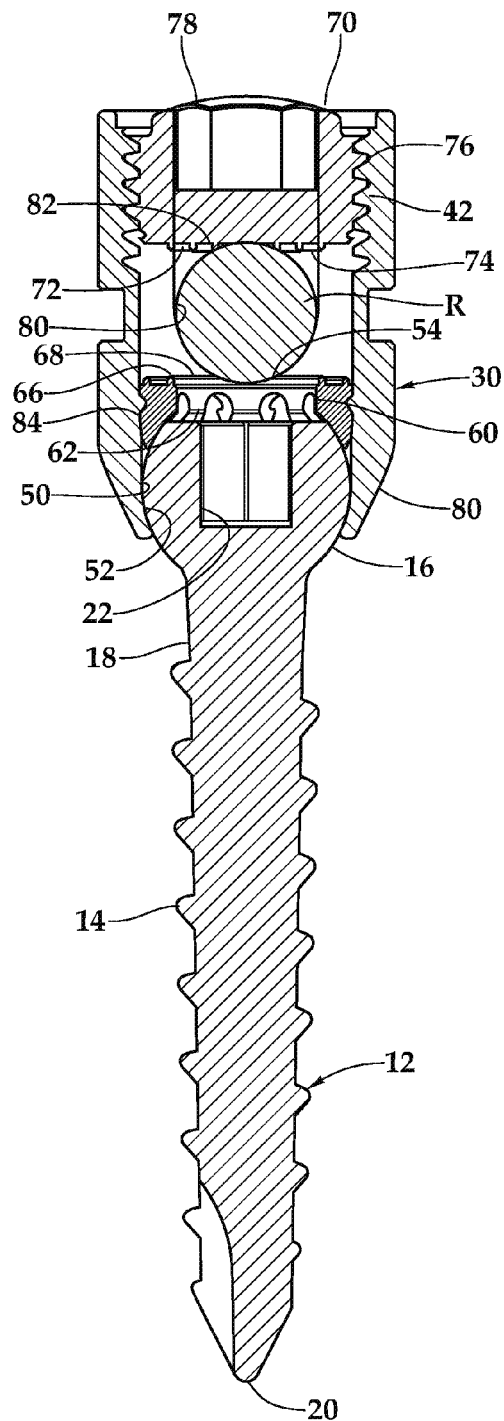
FIG. 11 is a side cross-sectional view of the pedicle screw system depicted in FIG. 2 following the application of force.

With reference to FIG. 11, the set screw 70 continues to be driven through the internal threads 42 for applying a downward force on the orthopedic rod R, which, in turn, provides a downward force on the face of the coupling collar 60. As the set screw 70 continues to advance, substantially simultaneously the collapsible rings 74 of at lower end of the set screw 70 and the collapsible rings 68 near the face of the coupling collar 60 deform and expand to conform to the shape of the orthopedic rod R.

As a result, the deformed surface of the coupling collar 60 expands to fill the receiving space 54, thereby engaging the spherical head 16 of the pedicle screw 12, the interior housing 32 of the tulip 30, and the orthopedic rod R in order to lock the tulip 30 in place relative to the pedicle screw 12 and preventing further pivotal movement of the tulip 30 relative to the pedicle screw 12. The force provided by the set screw 70 does not cause the head 16 of the pedicle screw 12 to be pressed against the interior housing 32 of the tulip 30. Rather, the force provided by the set screw 70 through the orthopedic rod R causes the deformation of the coupling collar 60 and pressing of the coupling collar 60 against the interior housing 32 of the tulip 30 and the pedicle screw 12 within the space therebetween.

Similarly, the collapsible or deformable face 72 of the set screw 70 conforms to the orthopedic rod R, thereby providing an engagement between the orthopedic rod R and the set screw 70. The deformed surface of the set screw 70 expands to fill receiving space 82, thereby creating an engagement. Moreover, in one embodiment, in a similar manner, the coupling collar 60 defines and expands to improve the conformed fit 84 between the coupling collar 60 and the seat 50 of the tulip 30. In this way, the orthopedic rod R, the tulip 30, and the pedicle screw 12 are fixed.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A pedicle screw fixation system comprising:
   a receiving member having a housing for receiving a pedicle screw having a head, the housing including a housing bore at a first end of a longitudinal axis and an opening at a second end of the longitudinal axis;
   the opening configured to receive a rod;
   a shaped seat formed within the housing, the shaped seat adapted to accept the head of the pedicle screw;
   a coupling collar including a plurality of resilient fingers circumferentially disposed therearound, the coupling collar adapted to engage with the head of the pedicle screw, the coupling collar having a surface of engagement including a first deformable face opposite to the plurality of resilient fingers the surface of engagement of the coupling collar being beneath a rod receiving space, the surface of engagement being configured to accept a downward force on the first deformable face to deform the first deformable face;
   a window extending through the coupling collar; and
   a set screw for threadably engaging the internal threads, an upper end of the set screw including a socket and a lower end of the set screw presenting a second deformable face.

2. The pedicle screw fixation system as recited in claim 1, wherein the housing further comprises a shaped seat adapted to a conformed fit with the coupling collar.

3. The pedicle screw fixation system as recited in claim 1, wherein the rod further comprises an unthreaded tubular rod.

4. The pedicle screw fixation system as recited in claim 1, wherein the shaped seat provides a universal point of contact.

5. The pedicle screw fixation system as recited in claim 1, wherein the shaped seat further comprises a receiving space thereabout to permit some angular displacement of the receiving member about the pedicle screw.

6. The pedicle screw fixation system as recited in claim 1, wherein the first deformable face of the coupling collar further comprises a pair of collapsible rings.

7. The pedicle screw fixation system as recited in claim 1, wherein the second deformable face of the set screw further comprises three collapsible rings.

8. The pedicle screw fixation system as recited in claim 1, wherein the window is sized to accept a tool that engages the socket.

9. A pedicle screw fixation system comprising:
   a tulip for holding a head of a pedicle screw substantially along a longitudinal axis, the tulip configured to receive a rod; and
   a coupling collar including a plurality of resilient fingers circumferentially disposed therearound, the coupling collar adapted for engagement with the head of the pedicle screw, the coupling collar having a surface of engagement including a first deformable face operable for contact with the rod and opposite to the plurality of resilient fingers, the surface of engagement of the coupling collar being beneath a rod receiving space, the surface of engagement being configured to accept a downward force on the first deformable face to deform the first deformable face.

10. The pedicle screw fixation system as recited in claim 9, wherein the tulip for holding the head further comprises a receiving space thereabout to permit some angular displacement of the tulip about the pedicle screw.

11. The pedicle screw fixation system as recited in claim 9, wherein the rod is operable to be set in contact with the coupling collar.

12. The pedicle screw fixation system as recited in claim 9, wherein the head is located in isolated contact with respect to the rod.

13. The pedicle screw fixation system as recited in claim 9, wherein the coupling collar is interposed between the rod and the head.

14. The pedicle screw fixation system as recited in claim 9, wherein the coupling collar protects the head from damaging torque and force during installation of the pedicle screw.

15. The pedicle screw fixation system as recited in claim 9, wherein the first deformable face of the coupling collar further comprises a pair of collapsible rings.

16. A method for using a pedicle screw fixation system with a bone, the method comprising:

provide a tulip holding a head of a pedicle screw substantially along a longitudinal axis of the tulip, the tulip configured to receive a rod;

providing a coupling collar having a plurality of resilient fingers circumferentially disposed therearound in engagement with the head of the pedicle screw, the coupling collar having a first deformable face operable for contact with a rod and having a surface of engagement including the first deformable face opposite to the plurality of resilient fingers the surface of engagement of the coupling collar being beneath a rod receiving space, the surface of engagement being configured to accept a downward force on the first deformable face to deform the first deformable face;

securing the pedicle screw to the bone; and receiving the rod through the first and second receiving slots.

17. The method as recited in claim 16, wherein securing the pedicle screw to the bone further comprises:

inserting a tool into a socket formed in the head of the pedicle screw, the tool being inserted through a window extending through the coupling collar; and applying torque to secure the pedicle screw to the bone.

18. The method as recited in claim 16, wherein receiving the rod through the first and second receiving slots further comprises seating the rod in contact with the coupling collar.

* * * * *